(12) United States Patent
Assefa et al.

(10) Patent No.: US 9,234,854 B2
(45) Date of Patent: Jan. 12, 2016

(54) SINGLE FIBER NONCRITICAL-ALIGNMENT WAFER-SCALE OPTICAL TESTING

(71) Applicant: International Business Machines Corporation, Armonk, NY (US)

(72) Inventors: Solomon Assefa, Ossining, NY (US); Douglas M. Gill, South Orange, NJ (US); Jessie C. Rosenberg, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 102 days.

(21) Appl. No.: 13/836,054

(22) Filed: Mar. 15, 2013

(65) Prior Publication Data

US 2014/0268113 A1    Sep. 18, 2014

(51) Int. Cl.

| | | |
|---|---|---|
| *G01N 21/95* | (2006.01) | |
| *H01L 21/66* | (2006.01) | |
| *G01M 11/00* | (2006.01) | |
| *G01N 21/00* | (2006.01) | |
| *G01N 21/88* | (2006.01) | |
| *G09G 3/00* | (2006.01) | |
| *G02B 6/30* | (2006.01) | |
| *G02B 6/28* | (2006.01) | |
| *H01L 31/00* | (2006.01) | |
| *G02F 1/21* | (2006.01) | |

(52) U.S. Cl.
CPC ........... *G01N 21/9501* (2013.01); *G01M 11/33* (2013.01); *G01M 11/35* (2013.01); *G01N 21/00* (2013.01); *G01N 21/8806* (2013.01); *G09G 3/006* (2013.01); *H01L 22/12* (2013.01); *G01N 2201/088* (2013.01); *G02B 6/2813* (2013.01); *G02B 6/30* (2013.01); *G02F 2001/217* (2013.01); *G02F 2201/58* (2013.01); *H01L 31/00* (2013.01)

(58) Field of Classification Search
None
See application file for complete search history.

(56) References Cited

U.S. PATENT DOCUMENTS

| | | | |
|---|---|---|---|
| 4,357,533 | A | 11/1982 | Winslow |
| 5,142,517 | A | 8/1992 | Takahashi |
| 6,477,284 | B1 | 11/2002 | Oda et al. |
| 6,559,946 | B2 | 5/2003 | Davidson et al. |

(Continued)

FOREIGN PATENT DOCUMENTS

| | | |
|---|---|---|
| JP | 60028044 A | 2/1985 |
| JP | 60119679 A | 6/1985 |

OTHER PUBLICATIONS

C. Gunn, "Fully Integrated VLSI CMOS and Photonics 'Cmos Photonics'," 2007 IEEE Symposium on VLSI Technology, Jun. 12-14, 2007, pp. 6-9.

(Continued)

*Primary Examiner* — Gordon J Stock, Jr.
(74) *Attorney, Agent, or Firm* — Cantor Colburn LLP; Vazken Alexanian

(57) ABSTRACT

A method of determining a parameter of a wafer is disclosed. Light is propagated through a waveguide disposed in the wafer. A first measurement of optical power is obtained at a first optical tap coupled to the waveguide and a second measurement of optical power is obtained at a second optical tap coupled to the waveguide using a photodetector placed at a selected location with respect to the wafer. A difference in optical power is determined between the first optical tap and the second optical tap from the first measurement and the second measurement. The parameter of the wafer is determined from the determined difference in optical power.

11 Claims, 10 Drawing Sheets

(56) References Cited

U.S. PATENT DOCUMENTS

| | | |
|---|---|---|
| 6,714,300 B1 | 3/2004 | Rosencwaig et al. |
| 6,859,587 B2 | 2/2005 | Nikonov et al. |
| 7,109,739 B2 | 9/2006 | Gothoskar et al. |
| 7,245,795 B2 | 7/2007 | Walker et al. |
| 7,262,852 B1 | 8/2007 | Gunn, III et al. |
| 8,064,745 B2 | 11/2011 | Fortusini et al. |
| 8,391,656 B2 | 3/2013 | Mathal et al. |
| 2002/0154316 A1 | 10/2002 | Davidson et al. |
| 2002/0191887 A1 | 12/2002 | Bidnyk |
| 2003/0053765 A1 | 3/2003 | Oda et al. |
| 2003/0080766 A1 | 5/2003 | Fetterman et al. |
| 2003/0223672 A1 | 12/2003 | Joyner et al. |
| 2004/0264842 A1* | 12/2004 | Tsai et al. ............ 385/16 |
| 2005/0111779 A1 | 5/2005 | Joyner et al. |
| 2007/0047875 A1 | 3/2007 | Sezerman et al. |
| 2007/0110367 A1 | 5/2007 | Walker et al. |
| 2010/0278484 A1 | 11/2010 | Scheerlinck et al. |
| 2011/0123190 A1* | 5/2011 | Xia et al. ............ 398/25 |
| 2012/0027347 A1 | 2/2012 | Mathal et al. |
| 2012/0155806 A1 | 6/2012 | Doerr et al. |
| 2013/0042375 A1 | 2/2013 | Humphris et al. |
| 2014/0043050 A1* | 2/2014 | Stone et al. ............ 324/750.01 |

OTHER PUBLICATIONS

G. Masini, et al., "High-Speed, Monolithic CMOS Receivers with Ge on Si Waveguide Photodetectors," ECS Trans., vol. 16, Issue 10, 2008, pp. 601-608.

A. Mekis, et al., "A Grating-Coupler-Enabled CMOS Photonics Platform," IEEE Journal of Selected Topics in Quantum Electronics, vol. 17, Issue 3, 2011, pp. 597-608.

R. Soref, "The Past, Present, and Future of Silicon Photonics," IEEE Journal of Selected Topics in Quantum Electronics, vol. 12, Issue 6, Nov.-Dec. 2006, pp. 1678-1687.

* cited by examiner

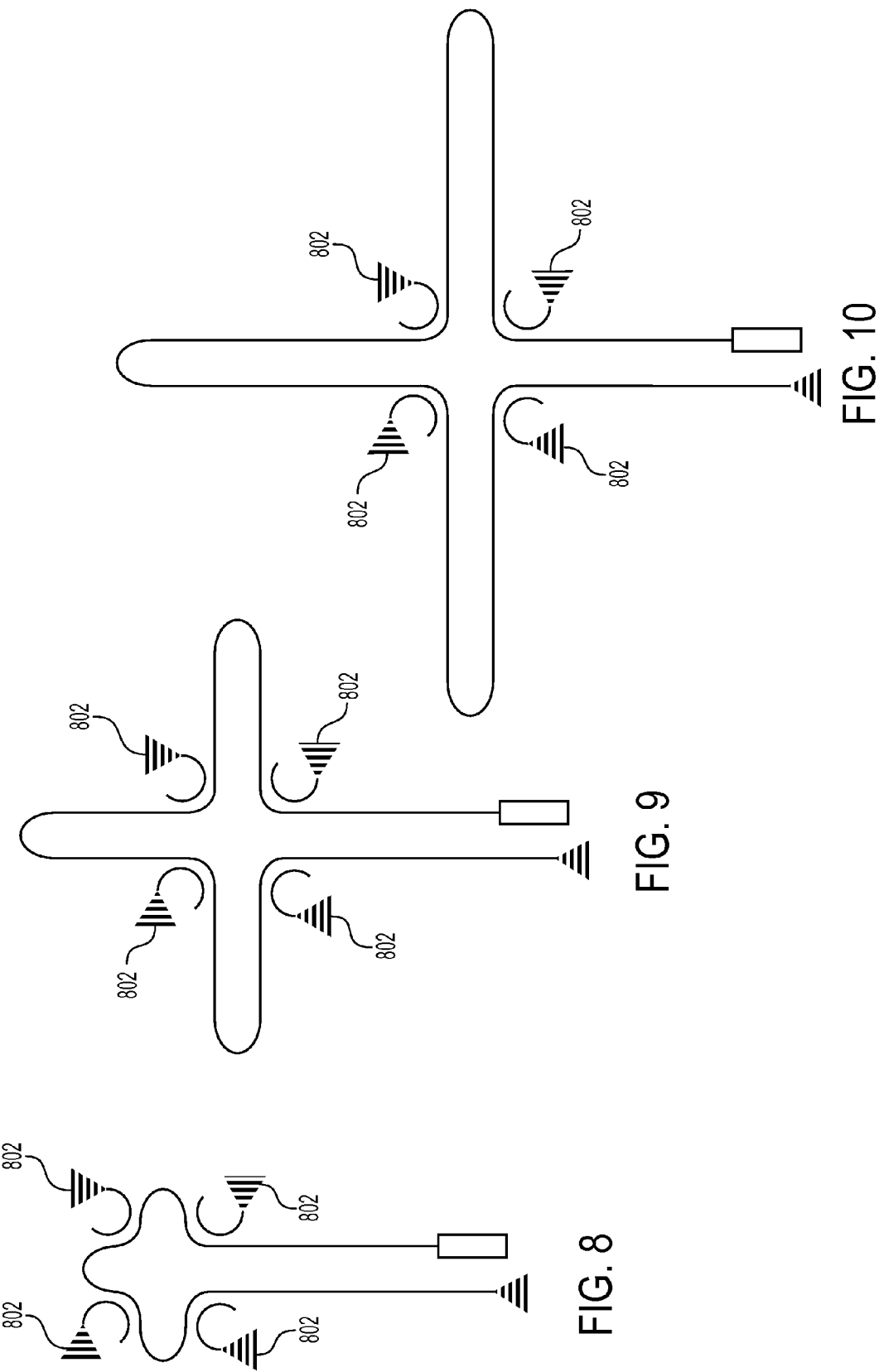

SINGLE FIBER NONCRITICAL-ALIGNMENT WAFER-SCALE OPTICAL TESTING

BACKGROUND

The present invention relates to wafer testing, and more specifically to optical testing of wafers in which optical alignment to input-output optical couplers is relaxed to increase wafer throughput.

Fabricating integrated electronic circuits on wafers includes a number of manufacturing stages. At any given stage, the wafer may be tested in order to identify defective components and/or chips. These wafers with defective components and/or chips may then be removed from the fabrication line to improve yield and reduce costs. One method of wafer testing includes optical testing. In an exemplary optical test, a waveguide is disposed in a silicon layer of the wafer. Light is input at an input end of the waveguide and exits at an output end of the waveguide. Changes in properties of the light during its travel through the waveguide provide a measurement of a parameter of the wafer or component that may be used to determine the quality of the wafer. Obtained optical measurements generally include on-chip optical loss (i.e., loss along the waveguide) and optical loss that occurs at both the input and output ends of the waveguide due to alignment issues between the waveguide and various input and/or output devices. Device parameters other than loss can also be measured, such as wavelength shift or phase shift. These parameters can be converted into a measured optical loss by a physical design of the test site on the wafer. While it is desirable to measure on-chip optical loss, it is difficult to determine how much of the measured loss is on-chip optical loss and how much is due to alignment issues with respect to input/output (IO) device coupling. Additionally, optical loss due to IO device coupling alignment often is greater than the measured on-chip optical component loss and so presents a significant measurement error, preventing repeatable measurements between test sites and over time.

SUMMARY

According to one embodiment of the present invention, a method of determining a parameter of a wafer includes: propagating light through a waveguide disposed at the wafer; obtaining a first measurement of optical power at a first optical tap coupled to the waveguide and a second measurement of optical power at a second optical tap coupled to the waveguide using a photodetector placed at a selected location with respect to the wafer; determining a difference in optical power between the first optical tap and the second optical tap from the first measurement and the second measurement; and determining the parameter of the wafer from the optical power loss.

According to another embodiment of the present invention, an optical wafer testing system includes: a waveguide configured to propagate an optical signal through the wafer; a first optical tap coupled to the waveguide at a first location; a second optical tap coupled to the waveguide at a second location; and a photodetector configured to obtain measurements of optical output power at the first optical tap and the second optical tap to measure a difference in optical power in the waveguide between the first optical tap and the second optical tap.

According to another embodiment of the present invention, a method of determining optical power loss in a wafer includes: propagating light through a waveguide disposed in the wafer, the waveguide having a first optical tap at a first location and a second optical tap at a second location; placing a photodetector at a selected location with respect to the wafer for receiving the optical power from the first optical tap at one segment of the photodetector and from the second optical tap at another segment of the photodetector; obtaining optical power measurements related to the first optical tap and the second optical tap at the photodetector; determining a difference in optical power between the first optical tap and the second optical tap using the optical power measurements; and determining the optical power loss from the determined difference in optical power.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter that is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 8-10 show optical waveguides having varying waveguide branch lengths that may be used to calibrate losses due to waveguide bends, optical propagation loss, and directional couplers;

DETAILED DESCRIPTION

Figure 1:
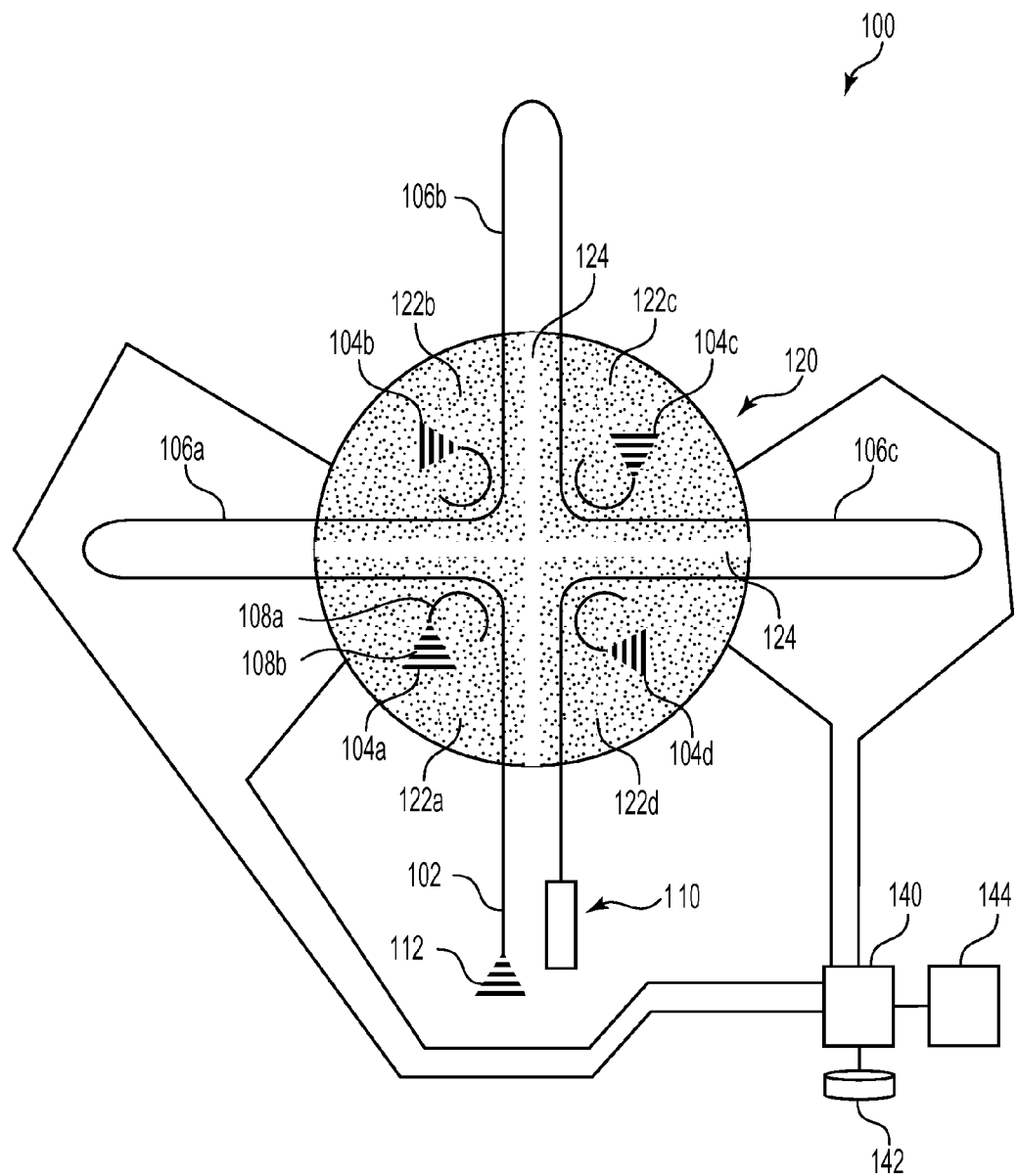
FIG. 1 shows an exemplary optical wafer testing system in one embodiment of the present disclosure.

FIG. 1 shows an exemplary optical wafer testing system 100 in one embodiment of the present disclosure. The exemplary optical wafer testing system 100 includes an optical waveguide 102 disposed in a layer of a wafer for propagating light or an optical signal through the wafer layer to one or more components or devices within the wafer layer. The optical waveguide 102 may include an input optical grating coupler 112 for coupling to an external fiber optic cable or other external device that delivers an optical signal into the optical waveguide 102. Additionally, an absorbent medium 110, such as a germanium absorber may be disposed at an end of the optical waveguide 102 distal to the input optical grating coupler 104 in order to minimize ambient scattered light from the output of the optical waveguide 102. Exemplary optical taps 104*a*, 104*b*, 104*c* and 104*d* are disposed at several locations with respect to the optical waveguide 102. The optical taps 104*a-d* may be built into the wafer and thus set at a permanent location with respect to the optical waveguide 102. The optical taps 104*a-d* remove a portion of light from the optical waveguide 102 at their respective locations in order to provide an optical power signal at their respective locations. In general, the optical taps 104*a-d* may include directional couplers for obtaining the optical power signal. Referring to optical tap 104*a* for illustrative purposes, in an exemplary embodiment, optical tap 104*a* may be an output optical grating coupler that includes a waveguide segment 108*a* coupled to an output grating 108*b*. The waveguide segment 108*a* of the output tap 104*a* is proximate the waveguide 102 at a selected distance such that a portion of the optical energy passing through the waveguide 102 is coupled into the waveguide segment 108*a*. The coupled optical energy in the waveguide segment 108*a* is output at output grating 108*b*. In general, the waveguide 102 is in a plane of the wafer and the optical taps 104*a-d* are oriented so as to direct the output energy in a direction out of the plane of the wafer and/or toward a detector.

An exemplary detector, such as photodetector 120, is shown at a measurement location with respect to the waveguide 102 and output taps 104*a*-104*d*. The wafer is generally moved into place relative to the photodetector 120 at the measurement location in order to be tested during a stage of the manufacturing process. A measurement may then be obtained and the wafer put back into the processing line in order to continue the manufacturing process or to a different location proximate another set of optical taps for further measurements. The photodetector 120 may be coupled to a processor 140 that may receive and store the voltages produced by the optical measurements or related applied or measured voltages from the sensor 120 and perform various calculations to determine an optical or electro-optic quality-metric parameter. The processor 140 may store the voltage measurements to a suitable storage medium 142, such as a physical memory location or to a display or monitor 144.

Photodetector 120 is shown at an exemplary testing location with respect to the wafer, and more specifically, with respect to the output taps 104*a*-104*d* of the wafer. The detecting area of the photodetector 120 is large compared to the area defined by optical taps 104*a*-104*d*. The photodetector 120 may be segmented into several segments or pixels, wherein a segment of the photodetector 120 is associated with an optical tap. In the exemplary embodiment, photodetector 120 is segmented into four quadrants 122*a*, 122*b*, 122*c* and 122*d*, associated with optical taps 104*a*, 104*b*, 104*c* and 104*d*, respectively. For example, photodetector segment 122*a* is associated with optical tap 104*a* and receives the optical power output provided by optical tap 104*a*. Although the photodetector 120 is shown as being segmented into quadrants, this is shown for illustrative purposes only. In various alternate embodiments, the photodetector 120 may be segmented into any number of segments, including eighths, sixteenths, etc. In general, the segmentation of the photodetector 120 is selected to accommodate a selected arrangement and number of optical taps. While the optical taps are shown herein in a quadrant formation, taps may also be arranged linearly or in any other suitable configuration. A selected segment of the photodetector 120 may be separated from other segments by light barriers 124 to prevent light from a selected optical tap from being received at a photodetector segment other than its associated photodetector segment. The light barriers 124 may be a physical barrier or an absence of detector material, thereby leaving a gap between detectors. The selection of the type of light barrier is dependent on a divergence angle of light from the optical couplers and the distance of the photodetector 120 to the wafer. Thus, light from optical tap 104*a*, for example, is prevented from being received at photodetector segments 122*b*, 122*c*, and 122*d*. The area of the photodetector 120 is large enough so that alignment of the optical taps 104*a*-104*d* with the photodetector segments 122*a*-122*d* is not a critical factor in measuring optical power output at the optical taps 104*a*-104*d*.

When the photodetector 120 is at its selected measurement location with respect to the optical taps 104*a*-104*d*, light from the optical taps 104*a*-104*d* creates a photocurrent in the photodetector 120. The photocurrent is then used to make a voltage that is measured to obtain a measurement of output power from the respective optical taps 104*a*-104*d*. In general, the photodetector is operated in a non-saturated mode so that the voltage produced by the light is proportional to the optical power received at the photodetector. In one embodiment, processor 140 may process the measurements of output power to determine optical power loss along a selected segment of the waveguide 102. In particular, the determined optical power loss may be a propagation loss in the waveguide 102, such as a propagation loss along waveguide branch 106*a*, waveguide branch 106*b* and/or waveguide branch 106*c*. Propagation loss along the waveguide branch 106*a* may be determined by a difference in measured output power at optical tap 104*b* and optical tap 104*a*. Propagation loss along waveguide branch 106*a* may be determined by a difference in measured output power at optical tap 104*c* and optical tap 104*b*. Propagation loss along waveguide branch 106*c* may be determined by a difference in measured output power at optical tap 104*d* and optical tap 104*c*. Additionally, the measurements obtained at the optical taps 104*a*-104*d* may be used to determined optical power loss related to devices located along any of the branches 106*a*-106*c*. These device-related optical power losses may be used to determine a quality control parameter of the device or other suitable parameter. For example, optical power may be measured as each of the optical taps 104*a-d* and plotting along a line, wherein the slope of the line gives the waveguide loss per unit length of propagation. This waveguide loss per unit length serves as a relevant control parameter.

Figure 2:
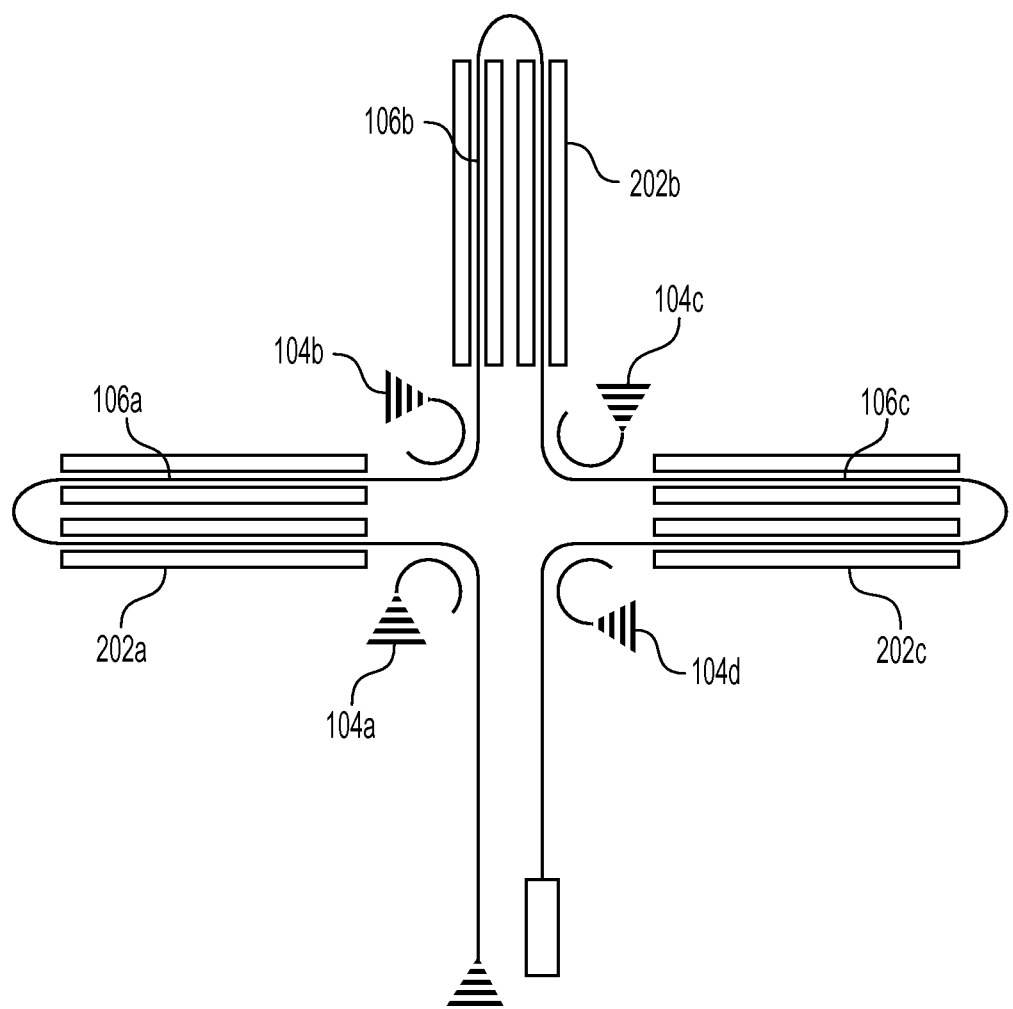
FIG. 2 shows exemplary p-n junctions disposed along respective waveguide branches of the optical testing system of FIG. 1.

FIG. 2 shows exemplary p-n junctions 202*a*-202*c* disposed along respective waveguide branches 106*a*-106*c* of the optical testing system 100 of FIG. 1. Although a photodetector and processor are not shown in FIG. 2 and various subsequent Figures, it may be understood that a photodetector may be positioned with respect to optical taps 104*a*-104*d* as shown in FIG. 1 in order to obtain optical power output measurements therefrom and similar calculations may be obtained using the processor. A selected waveguide branch 106*a* is positioned to run along an interface of the p-n junction 202*a*. Propagation of the optical signal in branch 106*a* of the optical waveguide 102 is affected by its proximity to the p-n junction 202*a*. Thus, differences in output power at the various taps 104*a*-104*c* may be used to determine an optical loss due to the p-n junctions 202a-202c. For example, a difference between a measurement of optical power output at optical tap 104a and 104b may be related to optical loss due to p-n junction 202a. In general, the p-n junctions 202a-202c are the same. Thus, their optical loss is generally determined by obtained measurements at the multiple taps 104a-104d. To measure different types of p-n junctions, additional test structures such as FIG. 2 are built for the selected p-n junction types. This optical loss may be used to determine a quality control parameter of the p-n junction 202a, which may be used to determine whether manufacture of the wafer continues or whether the wafer chip is defective. Although a p-n junction is shown in FIG. 2 for illustrative purposes, it is understood that any device may be tested in place of a p-n junction using the methods disclosed herein. In the exemplary embodiment of FIG. 2, the p-n junctions 202a-202c do not have a voltage bias applied to them.

Figure 3:
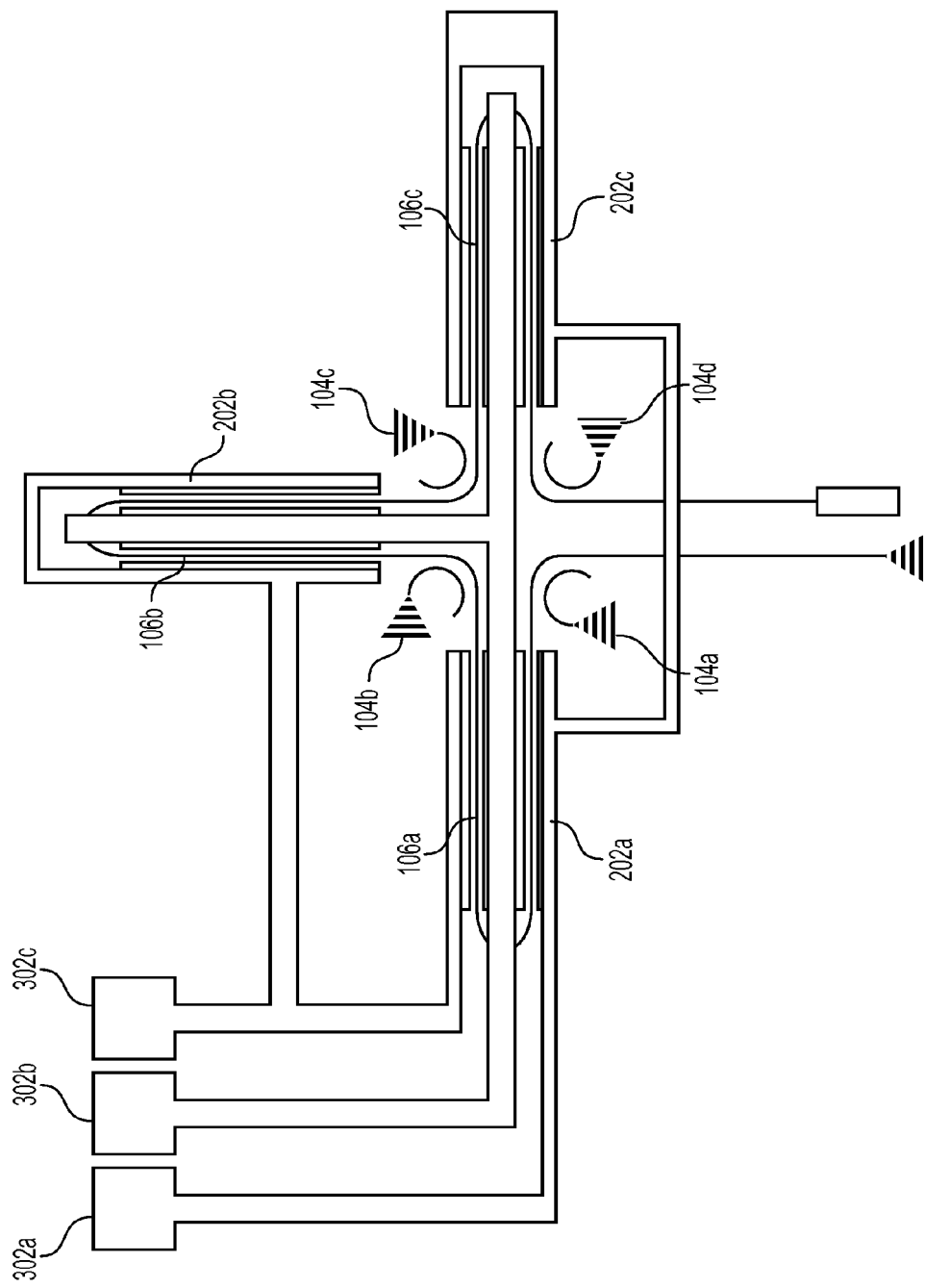
FIG. 3 shows the p-n junctions of FIG. 2 with a set of electrodes attached to apply a voltage bias.

FIG. 3 shows the p-n junctions 202a-202c of FIG. 2 with a set of electrodes 302a-302c coupled to the p-n junctions 202a-202c to apply a voltage bias. In alternate embodiments, the exemplary electrodes 302a-302c may be coupled to the p-n junctions 202a-202c in any suitable configuration. Various electrical leads may be brought into contact with the electrodes to 302a-302c in order to apply the voltage bias across the p-n junctions 202a-202c. The voltage bias may be applied in any combination. When the applied voltages induce a bias voltage in the p-n junctions 202a-202c, a parameter of an optical signal propagating in respective waveguide branches 106a-106c is altered. Thus, the operation of the p-n junction 202a-202c may be tested by measuring the optical power outputs with various voltage biases applied.

Figure 4:
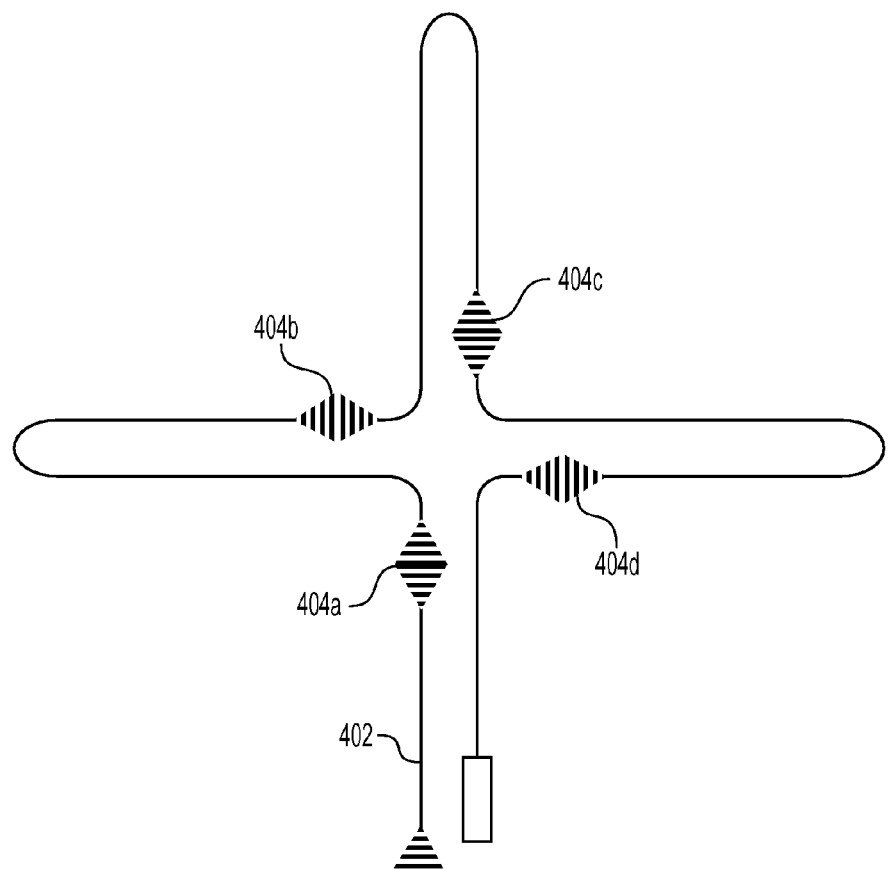
FIG. 4 shows an alternate embodiment for obtaining optical power output measurements from of an optical waveguide.

FIG. 4 shows an alternate embodiment for obtaining optical power output measurements from an optical waveguide 402. Optical waveguide 402 includes in-line gratings 404a-404d that are optical input-output coupling gratings serving as the optical taps. The in-line gratings 404a-404d may be placed at any selected location and may direct light toward photodetector 420 for measurement purposes. The in-line gratings 404a-404d therefore take the place of the direction couplers 104a-104d of FIG. 1.

Figure 5:
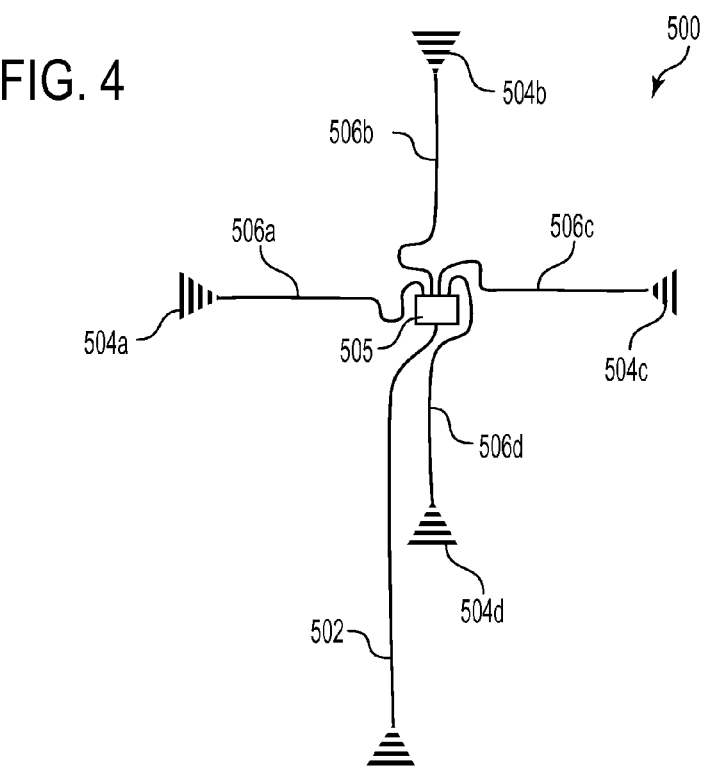
FIG. 5 shows an alternate optical loss measurement system of the present invention.

FIG. 5 shows an alternate optical loss measurement system 500 of the present invention embodiments. In the alternate embodiment, input waveguide 502 provides an input optical signal to a multi-mode interference splitter 505. The exemplary multi-mode interference (MMI) splitter 505 is a 1×4 MMI splitter that divides the input signal among the four outgoing waveguide branches 506a-506d. In various embodiments, the multi-mode interference splitter 505 is designed to divide the input optical signal evenly among the four waveguide branches 506a-506d. However, any selected division of the optical signal may be used. The output signals may be output at output taps 504a-504d to be measured at an exemplary photodetector placed with respect to the optical taps 504a-504d. The measurements of the output signals may be used to calibrate the MMI splitter 505 or to test its efficacy, i.e., its ability to evenly divide the input optical signal among the four waveguide branches 506a-506d. Additionally, the layout of FIG. 5 may be used as an alternate design to the layouts of FIG. 1-3. Alternatively, MMI splitters having 1×2, 1×8, 1×16 splitter ratios, etc., may also be calibrated using a suitable photodetector that is correspondingly segmented.

Figure 6:
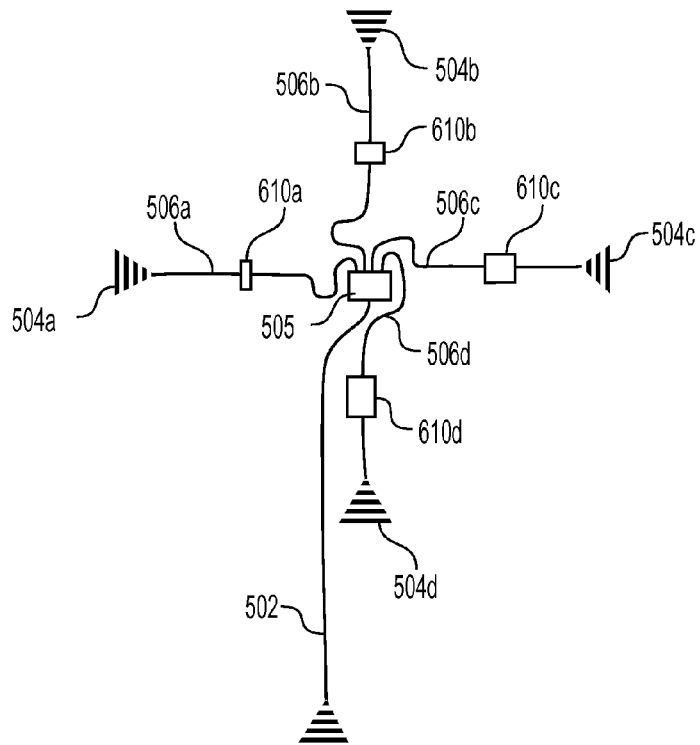
FIG. 6 shows the alternate optical loss measurement system of FIG. 5 configured to determine optical absorption per length of a selected material.

FIG. 6 shows the alternate optical loss measurement system of FIG. 5 configured to determine optical absorption per length of a selected material. In the exemplary embodiment, optical elements 601a-601d are embedded in the output waveguides 506a-506d. The optical elements 601a-601d may have selected lengths. For example, element 601a may have a length of 10 micrometers, element 601b may have a length of 20 micrometers, element 601c may have a length of 30 micrometers and element 601d may have a length of 40 micrometers. The optical loss measured at the output couplers 504a-504d may be used to determine an optical parameter, such as absorption or optical coupling, of each of the optical elements 601a-601d in the waveguide branches 506a-506d. Differences between these determined optical parameters may provide, for example, absorption per unit length of the optical element.

Figure 7:
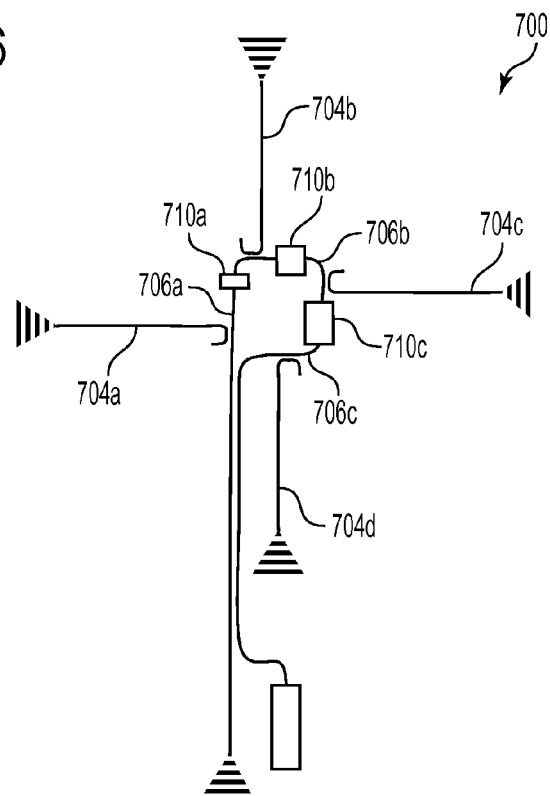
FIG. 7 shows an optical testing system for determining absorption of various optical elements using directional couplers.

FIG. 7 shows an optical testing system 700 for determining absorption of various optical elements 710a-710c using directional couplers 704a-704d. The optical elements 710a-710c are located along the waveguide branches 706a-706c. Optical loss generated by the optical elements 710a-710c may be determined from differences in the measurements obtained using the direction couplers 704a-704d. In various embodiments, the optical elements may include germanium elements. The length of the germanium elements may be varied in order to extract various absorption spectra. Alternately, the length of the germanium medium may be held fixed and the width varied in order to extract a coupling constant between the germanium element and silicon of the wafer chip.

FIGS. 8-10 show optical waveguides having varying waveguide branch lengths that may be used for calibration purposes. In each successive figure, the length of the optical waveguide branches between the optical taps 802 increase in length. Optical parameters such as coupler variability and measurement accuracy may be obtained by measuring a selected location using a plurality of the waveguides as shown in FIG. 8-10 having the differing waveguide branches lengths. A typical variation in branch length for a simple waveguide would probably be on the order of 2 to 10 mm between FIGS. 8-10.

The FIG. 8-10 are a set of example calibration structures for a particular test site layout. In addition to the waveguide length, there are additional sources of loss in the layouts, i.e., the directional couplers and the waveguide bends. The structures of FIGS. 8-10 help to calibrate out the loss due to the bends vs. the loss due to waveguide length. In FIG. 8, there are hardly any straight waveguide sections and the main loss is therefore from the bends. In FIGS. 9 and 10, the same bends are there while the straight sections have increased in length. The constant loss due to the bends can be subtracted from the loss of the straight waveguides. Thus, the effect of loss due to bends may be determined and subtracted out of future measurements.

Figure 11:
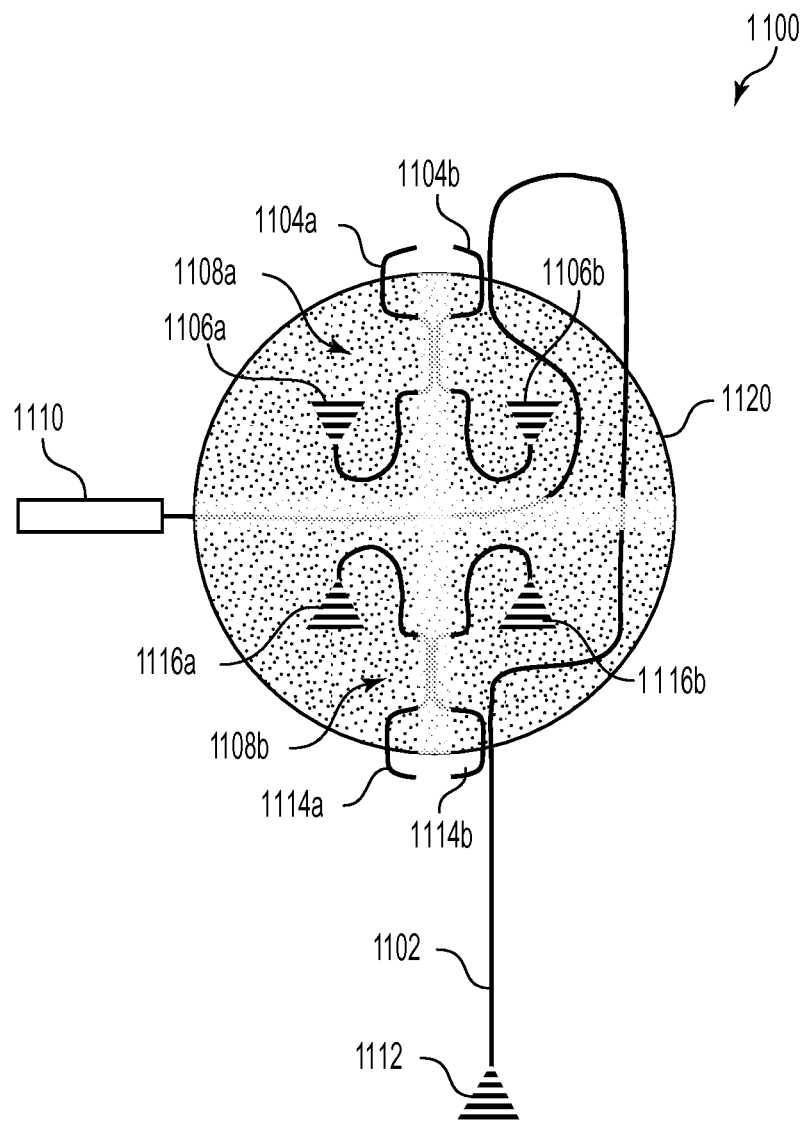
FIG. 11 shows an exemplary apparatus for testing directional couplers using the exemplary methods disclosed herein.

FIG. 11 shows an exemplary apparatus 1100 for testing directional couplers using the exemplary methods disclosed herein. The exemplary apparatus includes an optical waveguide 1102 having an input optical grating 1112 at one end for receiving an optical signal and an absorbent medium 1110, such as a germanium absorber, at an opposite end to minimize ambient scattered light. In the exemplary embodiment, two directional couplers 1108a and 1108b are shown. In alternate embodiments, any suitable number of directional couplers may be used. Exemplary directional coupler 1108a includes two optical waveguides 1104a and 1104b that are placed proximate each other to enable optical power transfer between them. Output optical grating coupler 1106a is coupled to optical waveguide 1104a for directing light in optical waveguide 1104a towards the photodetector 1120. Similarly, output optical grating coupler 1106b is coupled to optical waveguide 1104b for directing light in optical waveguide 1104b toward the photodetector 1120. In an exemplary embodiment, the optical waveguide 1104b is coupled to waveguide 1102 (via a directional coupler) to draw an optical signal from the waveguide 1102. Directional coupler 1108b similarly includes optical waveguides 1114a and 1114b coupled to output optical grating couplers 1116a and 1116b and is similarly coupled to the waveguide 1102 (via a directional coupler) to draw an optical signal from the waveguide 1102. The output optical grating couplers 1106a, 1106b, 1116a and 1116b are arrange to provide optical signals to the photodetector 1120 such that each signal is received at the photodetector at a corresponding quadrant of the photodetector 1120. Therefore, measurements obtained at the photodetector may be used to determine coupling coefficients of the directional couplers 1108a and 1108b, including the coupling coefficients between optical waveguides 1104a and 1104b and between optical waveguides 1114a and 1114b, for example. Although the optical grating couplers 1106a, 1106b, 1116a and 1116b are shown in a quadrant configuration, in alternate embodiments, there may be any number of optical grating couplers in any number of segments of a circle or other shape including in a linear configuration.

Figure 12:
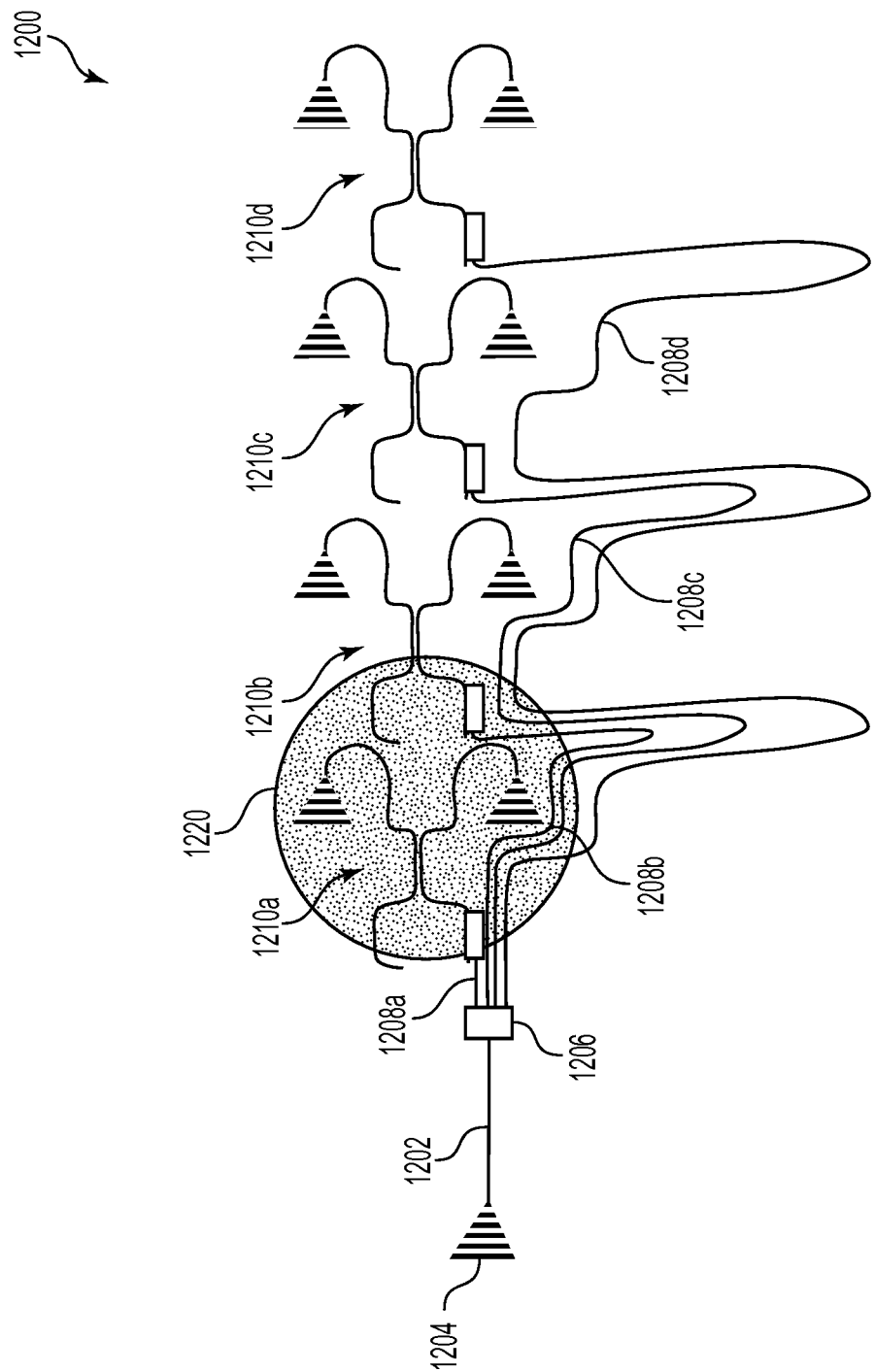
FIG. 12 shows an exemplary optical testing apparatus for measuring direction coupler loss and coupling coefficients and optical loss between couplers.

FIG. 12 shows an exemplary optical testing apparatus 1200 for simultaneously measuring direction coupler coupling coefficients and optical waveguide propagation loss between couplers. The apparatus 1200 includes an input waveguide 1202 having an input optical grating coupler 1204 at an input end and which is coupled to a 1×4 MMI splitter 1206. Optical waveguides 1208a-1208d extend from the MMI splitter 1206 to absorbent media that minimize ambient scattered light. Each of the optical waveguides 1208a-1208d is of a selected length and are coupled to respective directional couplers 1210a-1210d. In the exemplary apparatus 1200, optical waveguide 1208a is the shortest and optical waveguides 1208d is the longest. A photodetector 1220 may be moved into proximity of any of the directional couplers (for example, couplers 1210a and 1210b, as shown) to obtain suitable optical output measurements. Coupling coefficients of the directional couplers 1210a-1210d can be obtained from the optical output measurements. In addition, a summation of the power received from the grating couplers in each section, i.e., the directional coupler 1210a, the optical loss may be determined for each section. Plotting the optical losses at each of the grating couplers results in four points traced along a linear path, giving optical loss vs. waveguide length. Therefore, loss per unit length of the waveguide may be measured.

Figure 13:
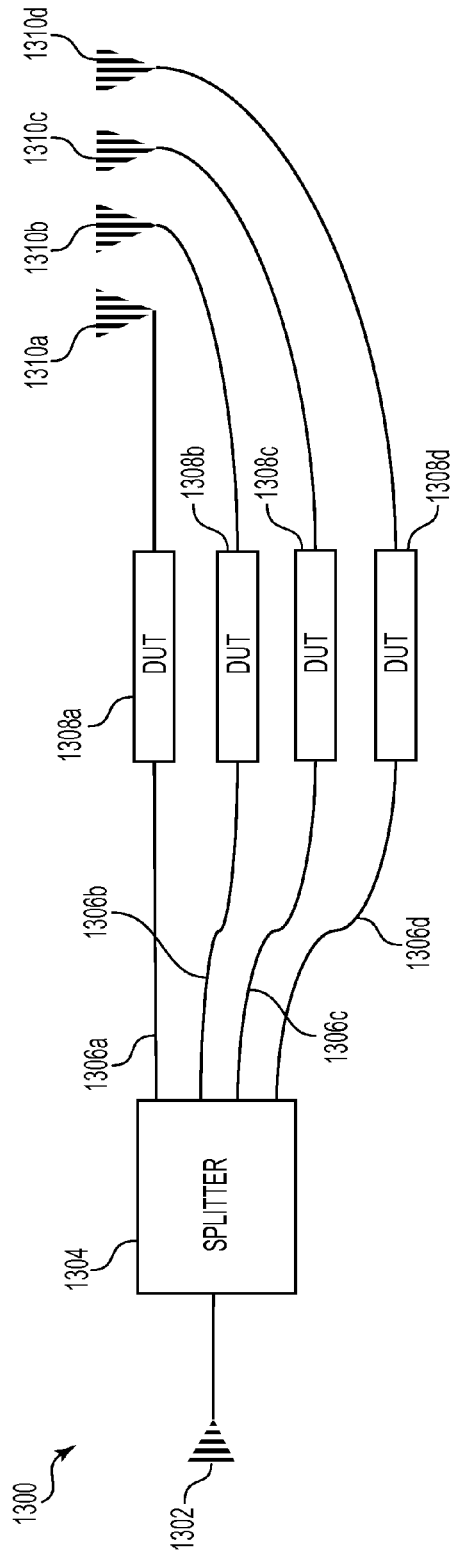
FIG. 13 shows an alternate optical loss measurement system of the present invention.

FIG. 13 shows an alternate optical loss measurement system 1300 of the present invention. A single optical fiber input 1302 is provided to splitter 1304. In the exemplary embodiment, the splitter 1304 splits the incoming light into four separate waveguides 1306a-d which direct light respectively to DUTs 1308a-d. The output of the DUTs 1308a-d propagates to optical pads 1310a-d which are aligned in a linear arrangement. A suitable photodetector may be a linearly-segmented photodetector arranged in the manner of the optical pads 1310a-d. The DUTs may be devices that do not use electrical contacts. The DUTs 1308a-d may be of different lengths of waveguide, have a different number of bends, lengths of p-n junctions, etc.

Figure 14:
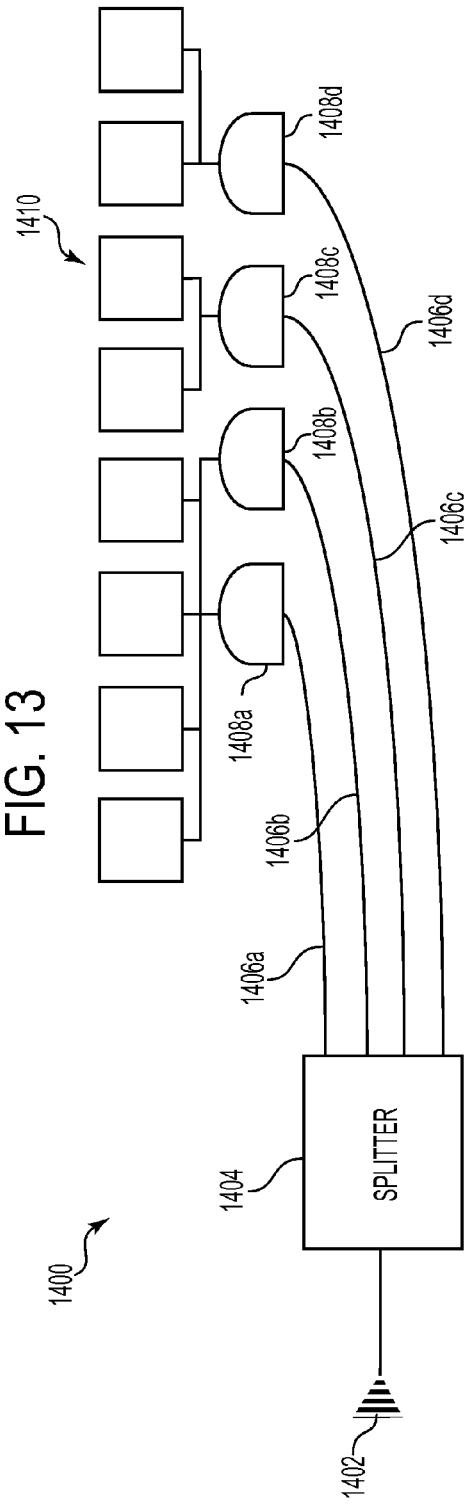
FIG. 14 show an alternate optical loss measurement system for testing detectors using optical inputs and electrical inputs.

FIG. 14 show an alternate optical loss measurement system 1400 for testing detectors using optical inputs and electrical inputs. A single optical fiber input 1402 is provided to splitter 1404. The splitter 1404 splits the incoming light into four separate waveguides 1406a-d which direct the light respectively to DUTs 1408a-d. The DUTs 1408a-d may be germanium detectors, in an exemplary embodiment. If a performance of a selected set of DUTs 1408a-d is known, the measurements obtained of the DUTs 1408a-d using the optical loss measurement system 140 may be used as a calibration of the system 140 for other DUT measurements. The output of each of the DUTs 1408a-d is sent to a pair of electrical pads 1410, which may be linearly arranged. The arrangement of FIG. 14 may be used to test germanium detector responsivity and therefore to compare responsivity between the detectors.

Figure 15:
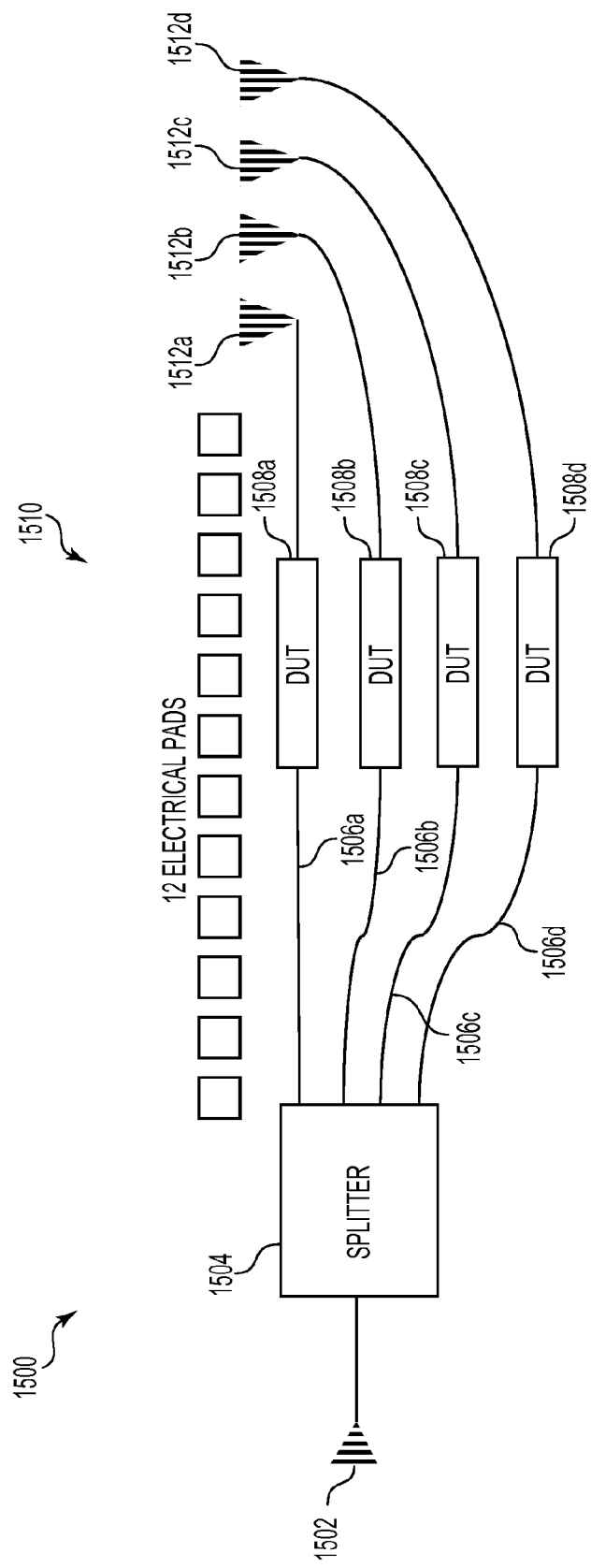
FIG. 15 shows another exemplary arrangement for testing electrically-active optical devices.

FIG. 15 shows another exemplary arrangement 1500 for testing electrically active optical devices, such as p-n junctions. In one embodiment, the arrangement 1500 may be used to measure p-n junction loss vs. applied bias. In an alternate embodiment, the arrangement 1500 may be used to measure phase shift of the p-n junctions. A single optical fiber input 1502 is provided to optical splitter 1504. The optical splitter 1504 splits in the incoming light into four separate waveguides 1506a-d which direct the light respectively to DUTs 1508a-d. The DUTs 1508a-d are coupled to electrical pads 1510 which may be used to modify a parameter of the DUTs 1508a-d. Optical output from the DUTs 1508a-d is directed to respective optical pads 1512a-d, which may be linearly arranged. Thus, electrical responsivity and optical properties may be measured simultaneously. In various embodiments, the DUTs 1508a-d may be modulators which may have different dopant profiles, lengths, geometry, etc. Thus, optical loss may be measured under different bias conditions, extinction ratios, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for exemplary embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method of determining a parameter of a wafer, comprising:

moving the wafer to a measurement location, wherein the wafer includes a waveguide disposed therein, a first optical tap coupled to the waveguide and a second optical tap coupled to the waveguide, and the measurement location includes a photodetector having a photodetecting area having a first segment of the photodetecting area that receives light from the first optical tap and a second segment of the photodetecting area that receives light from the second optical tap when the wafer is moved to the measurement location;

propagating light through the waveguide;

obtaining a first measurement of optical power at the first optical tap using the first segment of the photodetecting area and a second measurement of optical power at the second optical tap using the second segment of the photodetecting area at the measurement location;

determining a difference in optical power in the waveguide between the first optical tap and the second optical tap from a difference between the first measurement and the second measurement; and determining the parameter of the wafer from the difference in the optical power.

2. The method of claim 1, further comprising separating the first segment of the photodetecting area and the second segment of the photodetecting area using a light barrier at the photodetector area.

3. The method of claim 1, wherein at least one of the first and second optical taps comprises a pair of output gratings coupled to the waveguide via a directional coupler and the determined parameter includes a coupling coefficient of the directional coupler.

4. The method of claim 1, wherein the determined parameter further comprises a quality control parameter of the wafer.

5. The method of claim 1, wherein at least one of the first and second optical taps further comprises an optical tap selected from at least one of: a directional optical coupler, an optical input-output grating and a multi-mode interference splitter.

6. The method of claim 1, wherein the photodetecting area of the photodetector substantially covers an area defined by the first optical tap and the second optical tap when the wafer is moved to the measurement location to reduce a criticality of alignment of the photodetector with respect to the wafer.

7. The method of claim 1 wherein the determined parameter further comprises a propagation loss of a portion of the waveguide between the first optical tap and the second optical tap.

8. The method of claim 7, wherein the propagation loss further comprises an optical power loss related to at least one of: a splitting ratio of a directional coupler; an electronic device in the wafer, a PN junction associated with the portion of the waveguide between the first optical tap and the second optical tap, a voltage bias applied across the PN junction, and a medium disposed in the portion of the waveguide between the first optical tap and the second optical tap.

9. A method of determining optical power loss in a wafer, comprising:

moving the wafer to a measurement location, wherein the wafer includes a waveguide disposed therein, a first optical tap coupled to the waveguide and a second optical tap coupled to the waveguide, and the measurement location includes a photodetector having a photodetecting area having a first segment of the photodetecting area that receives light from the first optical tap and a second segment of the photodetecting area that receives light from the second optical tap when the wafer is moved to the measurement location;

propagating light through the waveguide;

receiving light from the first optical tap at the first segment of the photodetecting area and light from the second optical tap at the second segment of the photodetecting area;

obtaining optical power measurements related to the light from the first optical tap and the light from the second optical tap;

determining a difference in optical power between the first optical tap and the second optical tap using the optical power measurements; and determining the optical power loss from the determined difference in optical power.

10. The method of claim 9, further comprising separating the first segment of the photodetecting area and the second segment of the photodetector area using a light barrier at the photodetecting area.

11. The method of claim 9, wherein determining the optical power loss further comprises determining a quality control parameter of the wafer.

* * * * *